United States Patent
Carrara et al.

(10) Patent No.: US 8,980,309 B2
(45) Date of Patent: Mar. 17, 2015

(54) TRANSDERMAL TESTOSTERONE FORMULATION FOR MINIMIZING SKIN RESIDUES

(75) Inventors: Dario Norberto R. Carrara, Oberwil (CH); Arnaud Grenier, Steinbrunn-le-Haut (FR)

(73) Assignee: Antares Pharma IPL AG, Zug (CH)

( * ) Notice: Subject to any disclaimer, the term of this patent is extended or adjusted under 35 U.S.C. 154(b) by 573 days.

(21) Appl. No.: 13/106,530

(22) Filed: May 12, 2011

(65) Prior Publication Data

US 2011/0257141 A1 Oct. 20, 2011

Related U.S. Application Data

(63) Continuation of application No. 12/268,301, filed on Nov. 10, 2008, now abandoned, which is a continuation-in-part of application No. 11/755,923, filed on May 31, 2007, now abandoned, which is a continuation-in-part of application No. 11/371,042, filed on Mar. 7, 2006, now Pat. No. 7,335,379, which is a continuation of application No. PCT/EP2004/011175, filed on Oct. 6, 2004.

(60) Provisional application No. 60/510,613, filed on Oct. 10, 2003.

(51) Int. Cl.

| A61F 13/00 | (2006.01) |
|---|---|
| A61K 9/70 | (2006.01) |
| A61K 9/00 | (2006.01) |
| A61K 9/06 | (2006.01) |
| A61K 31/025 | (2006.01) |
| A61K 31/435 | (2006.01) |
| A61K 47/08 | (2006.01) |
| A61K 47/10 | (2006.01) |
| A61K 47/12 | (2006.01) |
| A61K 47/32 | (2006.01) |
| A61K 47/38 | (2006.01) |

(52) U.S. Cl.
CPC ............ *A61K 9/7007* (2013.01); *A61K 9/0014* (2013.01); *A61K 9/006* (2013.01); *A61K 9/06* (2013.01); *A61K 31/025* (2013.01); *A61K 31/435* (2013.01); *A61K 47/08* (2013.01); *A61K 47/10* (2013.01); *A61K 47/12* (2013.01); *A61K 47/32* (2013.01); *A61K 47/38* (2013.01); *Y10S 514/946* (2013.01); *Y10S 514/947* (2013.01)
USPC ............ 424/449; 424/400; 514/946; 514/947

(58) Field of Classification Search
USPC .......................... 424/449, 400; 514/946, 947
See application file for complete search history.

(56) References Cited

U.S. PATENT DOCUMENTS

| 2,990,332 A | 6/1961 | Keating ........................... 167/65 |
|---|---|---|
| 3,143,465 A | 8/1964 | Keating ........................... 167/65 |
| 3,891,696 A | 6/1975 | Bodor et al. ................... 560/142 |
| 3,989,816 A | 11/1976 | Rajadhyaksha ................. 424/60 |
| 4,082,881 A | 4/1978 | Chen et al. ....................... 514/39 |
| 4,221,778 A | 9/1980 | Raghunathan ................... 424/31 |
| 4,315,925 A | 2/1982 | Hussain et al. ................ 514/177 |
| 4,316,893 A | 2/1982 | Rajadhyakshan ............. 424/180 |
| 4,383,993 A | 5/1983 | Hussain et al. ................ 514/177 |
| 4,390,532 A | 6/1983 | Stuttgen et al. .................. 514/56 |
| 4,405,616 A | 9/1983 | Rajadhyaksha ................. 424/60 |
| 4,537,776 A | 8/1985 | Cooper .......................... 514/424 |
| 4,557,934 A | 12/1985 | Cooper .......................... 424/128 |
| 4,568,343 A | 2/1986 | Leeper et al. .................. 604/896 |
| 4,597,961 A | 7/1986 | Etscorn ........................ 424/448 |
| 4,704,406 A | 11/1987 | Stanislaus et al. ............ 514/570 |
| 4,764,381 A | 8/1988 | Bodor et al. ................... 424/449 |
| 4,783,450 A | 11/1988 | Fawzi et al. ...................... 514/78 |
| 4,808,411 A | 2/1989 | Lu et al. ......................... 424/441 |
| 4,832,953 A | 5/1989 | Campbell et al. ............. 424/448 |
| 4,863,970 A | 9/1989 | Patel et al. ..................... 514/784 |
| 4,883,660 A | 11/1989 | Blackman et al. ............... 424/78 |
| 4,952,560 A | 8/1990 | Kigasawa et al. ................. 514/2 |
| 4,956,171 A | 9/1990 | Chang .......................... 424/449 |
| 4,973,468 A | 11/1990 | Chiang et al. ................. 424/449 |
| 5,041,439 A | 8/1991 | Kasting et al. ............. 514/227.2 |
| 5,053,227 A | 10/1991 | Chiang et al. ................. 424/448 |
| 5,059,426 A | 10/1991 | Chiang et al. ................. 424/449 |
| 5,064,654 A | 11/1991 | Berner et al. ................. 424/448 |
| 5,071,657 A | 12/1991 | Oloff et al. ................... 424/486 |
| 5,112,842 A | 5/1992 | Zierenberg et al. ........... 514/367 |

(Continued)

FOREIGN PATENT DOCUMENTS

| EP | 0 249 397 A2 | 12/1987 |
|---|---|---|
| EP | 0 261 429 A1 | 3/1988 |

(Continued)

OTHER PUBLICATIONS 6,214,374, Apr. 2001, Schmirier et al. Withdrawn.

(Continued)

*Primary Examiner* — Ali Soroush
(74) *Attorney, Agent, or Firm* — Winston & Strawn LLP

(57) ABSTRACT

This invention relates to novel transdermal or transmucosal pharmaceutical formulation having an active agent of testosterone which reduces the occurrences of contamination of other individuals and the transference to clothing of the user. The solvent system of the formulation includes a monoalkylether of diethylene glycol and a glycol present in specified ratios, and a mixture of water and alcohol. The invention also relates to a method for inhibiting or delaying crystallization of the active agent in a pharmaceutical formulation.

11 Claims, 5 Drawing Sheets

(56) References Cited

U.S. PATENT DOCUMENTS

| | | | | |
|---|---|---|---|---|
| 5,128,138 | A | 7/1992 | Blank | 424/449 |
| 5,134,127 | A | 7/1992 | Stella et al. | 514/58 |
| 5,164,190 | A | 11/1992 | Patel et al. | 424/448 |
| 5,175,190 | A | 12/1992 | Burton et al. | 514/560 |
| 5,178,879 | A | 1/1993 | Adekunle et al. | 424/484 |
| 5,188,825 | A | 2/1993 | Hes et al. | 424/78.1 |
| 5,225,189 | A | 7/1993 | Pena | 424/70 |
| 5,230,896 | A | 7/1993 | Yeh et al. | 424/443 |
| 5,232,703 | A | 8/1993 | Blank | 424/449 |
| 5,238,933 | A | 8/1993 | Catz et al. | 514/236.2 |
| 5,278,176 | A | 1/1994 | Lin | 514/343 |
| 5,352,457 | A | 10/1994 | Jenkins | 424/448 |
| 5,371,005 | A | 12/1994 | Fujishiro et al. | 435/190 |
| 5,374,421 | A | 12/1994 | Tashiro et al. | 424/70.12 |
| 5,376,645 | A | 12/1994 | Stella et al. | 514/58 |
| 5,380,763 | A | 1/1995 | Sato et al. | 514/724 |
| 5,397,771 | A | 3/1995 | Bechgaard et al. | 514/2 |
| 5,453,279 | A | 9/1995 | Lee et al. | 424/448 |
| 5,527,832 | A | 6/1996 | Chi et al. | 514/772.4 |
| 5,532,278 | A | 7/1996 | Aberg et al. | 514/617 |
| 5,549,888 | A | 8/1996 | Venkateswaran | 424/78.02 |
| 5,552,153 | A | 9/1996 | Behl | 424/449 |
| 5,576,279 | A | 11/1996 | Pyles | 510/122 |
| 5,580,574 | A | 12/1996 | Behl et al. | 424/449 |
| 5,601,839 | A | 2/1997 | Quan et al. | 424/448 |
| 5,602,017 | A | 2/1997 | Fujishiro et al. | 435/190 |
| 5,603,947 | A | 2/1997 | Wong et al. | 424/449 |
| 5,629,021 | A | 5/1997 | Wright | 424/489 |
| 5,633,008 | A | 5/1997 | Osborne et al. | 424/448 |
| 5,658,587 | A | 8/1997 | Santus et al. | 424/448 |
| 5,660,839 | A | 8/1997 | Allec et al. | 424/401 |
| 5,662,890 | A | 9/1997 | Punto et al. | 424/59 |
| 5,665,560 | A | 9/1997 | Fujishiro et al. | 435/11 |
| 5,677,346 | A | 10/1997 | Aberg et al. | 51/617 |
| 5,716,638 | A | 2/1998 | Touitou | 424/450 |
| 5,719,197 | A | 2/1998 | Kanios et al. | 514/772.6 |
| 5,731,303 | A | 3/1998 | Hsieh | 514/183 |
| 5,736,577 | A | 4/1998 | Aberg et al. | 514/617 |
| 5,783,207 | A | 7/1998 | Stanley et al. | 424/440 |
| 5,785,991 | A | 7/1998 | Burkoth et al. | 424/448 |
| 5,786,357 | A | 7/1998 | Young et al. | 514/249 |
| 5,798,242 | A | 8/1998 | Fujishiro et al. | 435/190 |
| 5,814,659 | A | 9/1998 | Elden | 514/452 |
| 5,831,035 | A | 11/1998 | Timms | 530/389.1 |
| 5,834,010 | A | 11/1998 | Quan et al. | 424/448 |
| 5,843,482 | A | 12/1998 | Rhodes et al. | 424/653 |
| 5,846,983 | A | 12/1998 | Sandborn et al. | 514/343 |
| 5,855,905 | A | 1/1999 | Oettel et al. | 424/426 |
| 5,855,920 | A | 1/1999 | Chein | 424/568 |
| 5,891,462 | A * | 4/1999 | Carrara | 424/449 |
| 5,900,250 | A | 5/1999 | Lee et al. | 424/448 |
| 5,904,931 | A | 5/1999 | Lipp et al. | 424/449 |
| 5,922,349 | A | 7/1999 | Elliesen et al. | 424/449 |
| 5,925,372 | A | 7/1999 | Berner et al. | 424/448 |
| 5,932,243 | A | 8/1999 | Fricker et al. | 424/450 |
| 5,935,604 | A | 8/1999 | Illum | 424/501 |
| 5,945,405 | A | 8/1999 | Spanton et al. | 514/29 |
| 5,955,455 | A | 9/1999 | Labrie | 514/179 |
| 5,968,919 | A | 10/1999 | Samour et al. | 514/177 |
| 6,008,192 | A | 12/1999 | Al-Razzak et al. | 514/11 |
| 6,034,079 | A | 3/2000 | Sanberg et al. | 514/225.8 |
| 6,060,077 | A | 5/2000 | Meignant | 424/434 |
| 6,071,959 | A | 6/2000 | Rhodes et al. | 514/535 |
| 6,096,733 | A | 8/2000 | Lubkin | 514/182 |
| 6,123,961 | A | 9/2000 | Aberg | 424/468 |
| 6,124,355 | A | 9/2000 | Guittard et al. | 517/534 |
| 6,133,248 | A | 10/2000 | Stella | 514/58 |
| 6,153,216 | A | 11/2000 | Cordes et al. | 424/449 |
| 6,165,497 | A | 12/2000 | Osborne et al. | 424/448 |
| 6,166,044 | A | 12/2000 | Sandborn et al. | 514/343 |
| 6,180,803 | B1 | 1/2001 | Piasco et al. | 552/510 |
| 6,238,689 | B1 | 5/2001 | Rhodes et al. | 424/436 |
| 6,267,985 | B1 | 7/2001 | Chen et al. | 424/451 |
| 6,284,234 | B1 | 9/2001 | Niemiec et al. | 424/78.07 |
| 6,299,900 | B1 | 10/2001 | Reed et al. | 424/449 |
| 6,309,843 | B1 | 10/2001 | Timms | 435/7.1 |
| 6,319,913 | B1 | 11/2001 | Mak et al. | 514/179 |
| 6,383,471 | B1 | 5/2002 | Chen et al. | 424/45 |
| 6,417,205 | B1 | 7/2002 | Cooke et al. | 514/343 |
| 6,426,078 | B1 | 7/2002 | Bauer et al. | 424/401 |
| 6,432,446 | B2 | 8/2002 | Aberg | 424/468 |
| 6,440,454 | B1 | 8/2002 | Santoro et al. | 424/449 |
| 6,444,234 | B1 | 9/2002 | Kirby et al. | 424/725 |
| 6,451,300 | B1 | 9/2002 | Dunlop et al. | 424/70.27 |
| 6,465,005 | B1 | 10/2002 | Biali et al. | 424/449 |
| 6,476,012 | B2 | 11/2002 | Hochberg | 514/182 |
| 6,479,076 | B2 | 11/2002 | Blank | 424/484 |
| 6,497,897 | B2 | 12/2002 | Hidaka et al. | 424/449 |
| 6,503,894 | B1 | 1/2003 | Dudley et al. | 514/178 |
| 6,545,046 | B2 | 4/2003 | Sherratt et al. | 514/534 |
| 6,586,000 | B2 | 7/2003 | Luo et al. | 424/449 |
| 6,596,740 | B2 | 7/2003 | Jones | 514/343 |
| 6,743,441 | B2 | 6/2004 | Sanders et al. | 424/448 |
| 6,818,226 | B2 | 11/2004 | Reed et al. | 424/449 |
| 6,828,336 | B2 | 12/2004 | Walling | 514/343 |
| 6,911,475 | B1 | 6/2005 | Cesaro et al. | 514/567 |
| 6,923,983 | B2 | 8/2005 | Morgan et al. | 424/448 |
| 6,929,801 | B2 | 8/2005 | Klose et al. | 424/448 |
| 6,951,846 | B2 | 10/2005 | Hartell et al. | 514/58 |
| 6,995,265 | B2 | 2/2006 | Comins et al. | 546/14 |
| 7,029,692 | B1 | 4/2006 | Bracht | 424/449 |
| 7,030,104 | B2 | 4/2006 | Gray et al. | 514/170 |
| 7,087,241 | B2 | 8/2006 | Sanders et al. | 424/449 |
| 7,198,801 | B2 | 4/2007 | Carrara et al. | 424/449 |
| 7,214,381 | B2 | 5/2007 | Carrara et al. | 424/449 |
| 2001/0023261 | A1 | 9/2001 | Ryoo | 514/772 |
| 2001/0031787 | A1 | 10/2001 | Hsu et al. | 514/534 |
| 2001/0033870 | A1 | 10/2001 | Luo et al. | 424/688 |
| 2001/0038855 | A1 | 11/2001 | Desjardin et al. | 424/468 |
| 2002/0147236 | A1 | 10/2002 | Sanders et al. | 514/540 |
| 2002/0183296 | A1 * | 12/2002 | Dudley et al. | 514/177 |
| 2003/0022877 | A1 | 1/2003 | Dudley | 514/177 |
| 2003/0050292 | A1 | 3/2003 | Dudley et al. | 514/177 |
| 2003/0095926 | A1 | 5/2003 | Dugger, III | 424/43 |
| 2003/0139384 | A1 | 7/2003 | Dudley | 514/177 |
| 2003/0143278 | A1 | 7/2003 | DiPiano et al. | 424/489 |
| 2003/0147926 | A1 | 8/2003 | Ebert et al. | 424/400 |
| 2003/0175329 | A1 | 9/2003 | Azarnoff et al. | 424/449 |
| 2003/0181430 | A1 | 9/2003 | Gray et al. | 514/170 |
| 2003/0199426 | A1 | 10/2003 | Carrara et al. | 514/2 |
| 2003/0222105 | A1 | 12/2003 | Lee et al. | 222/382 |
| 2003/0232072 | A1 | 12/2003 | Dudley et al. | 424/449 |
| 2004/0002482 | A1 | 1/2004 | Dudley et al. | 514/169 |
| 2004/0139990 | A1 | 7/2004 | Wachter et al. | 134/25.4 |
| 2004/0198706 | A1 | 10/2004 | Carrara et al. | 514/169 |
| 2004/0213744 | A1 | 10/2004 | Lulla et al. | 424/45 |
| 2004/0219197 | A1 | 11/2004 | Carrara et al. | 424/449 |
| 2005/0142175 | A1 | 6/2005 | Langguth et al. | 424/449 |
| 2006/0027278 | A1 | 2/2006 | Kurmis | 140/123.5 |
| 2006/0153905 | A1 | 7/2006 | Carrara et al. | 424/449 |
| 2006/0270642 | A1 | 11/2006 | Lehman et al. | 514/170 |
| 2007/0048360 | A1 | 3/2007 | Carrara et al. | 424/443 |
| 2007/0098775 | A1 | 5/2007 | Carrara et al. | 424/449 |
| 2007/0166361 | A1 | 7/2007 | Carrara et al. | 424/448 |
| 2007/0225379 | A1 | 9/2007 | Carrara et al. | 424/449 |
| 2009/0069364 | A1 | 3/2009 | Carrara et al. | 514/284 |

FOREIGN PATENT DOCUMENTS

| | | |
|---|---|---|
| EP | 0 267 617 A1 | 5/1988 |
| EP | 0 271 983 A1 | 6/1988 |
| EP | 0 279 977 A2 | 8/1988 |
| EP | 0 367 431 A1 | 5/1990 |
| EP | 0 250 125 B1 | 9/1991 |
| EP | 0 526 561 B1 | 2/1993 |
| EP | 0 325 613 B1 | 9/1993 |
| EP | 0 672 422 A1 | 3/1994 |
| EP | 0 409 383 B1 | 4/1994 |
| EP | 0 435 200 B1 | 7/1995 |
| EP | 0 785 211 A1 | 7/1997 |
| EP | 0 785 212 A1 | 7/1997 |
| EP | 0 811 381 A1 | 12/1997 |
| EP | 0 491 803 B1 | 7/1999 |
| EP | 0 804 926 B1 | 10/1999 |

(56) References Cited

FOREIGN PATENT DOCUMENTS

| | | |
|---|---|---|
| EP | 0 655 900 B1 | 3/2000 |
| EP | 0 719 538 B1 | 11/2000 |
| EP | 0 814 776 B1 | 7/2001 |
| EP | 0 643 963 B1 | 11/2001 |
| EP | 0 868 187 B1 | 12/2001 |
| EP | 0 859 793 B1 | 2/2002 |
| EP | 1 089 722 B1 | 5/2002 |
| EP | 0 802 782 B1 | 2/2003 |
| EP | 1 323 430 A2 | 7/2003 |
| EP | 1 323 431 A2 | 7/2003 |
| EP | 1 325 752 A2 | 7/2003 |
| FR | 2 518 879 A1 | 12/1981 |
| FR | 2 776 191 A1 | 9/1999 |
| JP | 09-176049 A | 7/1997 |
| WO | WO 90/11064 A1 | 10/1990 |
| WO | WO 92/08730 A1 | 5/1992 |
| WO | WO 94/06437 A1 | 3/1994 |
| WO | WO 95/18603 A1 | 7/1995 |
| WO | WO 95/29678 A1 | 11/1995 |
| WO | WO 97/03676 A1 | 2/1997 |
| WO | WO 97/29735 A1 | 8/1997 |
| WO | WO 97/34607 A1 | 9/1997 |
| WO | WO 97/38726 A2 | 10/1997 |
| WO | WO 98/17316 A1 | 4/1998 |
| WO | WO 98/37879 A1 | 9/1998 |
| WO | WO 99/20257 A1 | 4/1999 |
| WO | WO 99/24041 A1 | 5/1999 |
| WO | WO 99/48477 A1 | 9/1999 |
| WO | WO 01/80796 A1 | 11/2001 |
| WO | WO 02/11768 A1 | 2/2002 |
| WO | WO-02/11768 A1 * | 2/2002 |
| WO | WO 02/22132 A2 | 2/2002 |
| WO | WO 02/17967 A1 | 3/2002 |
| WO | WO 2004/037173 A2 | 5/2004 |
| WO | WO 2004/080413 A2 | 9/2004 |
| WO | WO 2005/039531 A1 | 5/2005 |

OTHER PUBLICATIONS

Budavari et al., The Merk Index, 1996, Merck Research Laboratories, 12th Edition, pp. 253 and 269.

Kotiyan et al., "Eudragits:Role as crystallization inhibitors in drug-in-adhesive transdermal systems of estradiol," European Journal of Pharmaceutics and Biopharmaceutics 52: 173-180 (2001).

Lipp, "Selection and use of crystallization inhibitors for matrix-type transdermal drug-delivery systems containing sex steroids," J. Pharm. Pharmacol. 50: 1343-1349 (1998).

Moser et al., "Passive skin penetration enhancement and its quantification in vitro," European Journal of Pharmaceutics and Biopharmaceutics 52: 103-112 (2001).

Mura et al., "Evaluation of transcutol as a clonazepam transdermal permeation enhancer from hydrophilic gel formulations," European Journal of Pharmaceutical Sciences 9: 365-372 (2000).

D. Osborne et al., "Skin Penetration Enhancers Cited in the Technical Literature," Pharmaceutical Technology 1997, 21(11): 58-66.

R. Panchagnula et al., "Development and evaluation of an intracutaneous depot formulation of corticosteroids using transcutol as a cosolvent: in-vitro, ex-vivo and in-vivo rat studies," J. Pharm. Pharmacol. 1991, 43: 609-614.

L. Pavliv et al., "Topical formulation development of a novel thymidylate synthase inhibitor for the treatment of psoriasis," International Journal of Pharmaceutics 1994, 105: 227-233.

W.A. Ritschel et al., "In vitro skin penetration of griseofulvin in rat and human skin from an ointment dosage form," Arzneimittelforschung. 1988, 38(11): 1630-1632.

W.A. Ritschel et al., "Use of sorption promoters to increase systemic absorption of coumarin from transdermal drug delivery systems," Arzneimittelforschung. 1988, 38(12): 1774-1777.

W.A. Ritschel et al., "Development of an intracutaneous depot for drugs," Skin Pharmacol. 1991, 4:235-245.

J. Rojas, "Optimization of binary and ternary solvent systems in the percutaneous absorption of morphine base," S.T.P. Pharma Sciences 1991, 1(1): 70-75.

G. Stüttgen, "Promoting penetration of locally applied substances by urea," Hautarzt 1989; 40 Suppl 9:27-31 (abstract).

K. Takahashi et al., "Effect of Vehicles on Diclofenac Permeation across Excised Rat Skin," Biol. Pharm. Bull. 1995, 18(4): 571-575.

E. Touitou, "Enhanced permeation of theophylline through the skin and its effect on fibroblast proliferation," International Journal of Pharmaceutics 1991, 70: 159-166.

A. Watkinson, "Aspects of the transdermal delivery of prostaglandins," International Journal of Pharmaceutics 1991, 74: 229-236.

A.C. Williams et al., "Urea Analogues in Proplyene Glycol as Penetration Enhancers in Human Skin," International Journal of Pharmaceutics 1989, 36: 43-50.

M. Yazdanian et al., "The effect of diethylene glycol monoethyl ether as a vehicle for topical delivery of ivermectin," Veterinary Research Communications 1995, 19(4): 309-319.

P. Karande and S. Mitragotri, "High Throughput Screening of Transdermal Formulations," Pharmaceutical Research, 2002, 19(5): 655-660.

Oxytrol information sheet, Oxybutynin Transdermal System, Watson Pharma, Inc., Corona CA, 2 pages (Feb. 2003).

"New Drug Application: Elestrin, estradiol, Treatment for Postmenopausal Symptoms. BioSante Pharmaceuticals Announces Bio-E-Gel NDA Submission," Internet article, [online], Feb. 16, 2006; retrieved from the Internet: URL:http://www.drugs.com/nda/elestrin_060216.html (retrieved on Sep. 18, 2007).

J. Fang et al., XP-0007999490, "Effect of Adhesive and Drug reservoir on in vitro transdermal delivery of Nocotine," Pharmazie, Die, Govi Verlag, Eschborn, De, (1999), 54(2): 154-155.

Catherino et al., "Nomegestrol Acetate, a Clinically Useful 19-Norprogesterone Derivative which Lacks Estrogenic Activity," J. Steroid Biochem. Molec. Biol. 55(2):239-246 (1995).

Wang et al., "Transdermal Testosterone Gel Improves Sexual Function, Mood, Muscle Strength, and Body Composition Parameters in Hypogonadal Men," The Journal of Clinical Endocrinology & Metabolism 85(8):2839-2853 (2000).

www.rxlist.com (retrieved May 21, 2007).

U.S. Appl. No. 10/798,111, Non-Final Office Action dated Dec. 23, 2010.

U.S. Appl. No. 10/798,111, Non-Final Office Action dated Dec. 7, 2009.

U.S. Appl. No. 10/798,111, Final Office Action dated Mar. 4, 2009.

U.S. Appl. No. 10/798,111, Non-Final Office Action dated Sep. 15, 2008.

U.S. Appl. No. 10/798,111, Non-Final Office Action dated Jun. 4, 2007.

U.S. Appl. No. 10/798,111, Non-Final Office Action dated Jan. 25, 2006.

U.S. Appl. No. 10/798,111, Non-Compliant Office Action dated Sep. 27, 2007.

U.S. Appl. No. 10/798,111, Final Office Action dated May 20, 2010.

U.S. Appl. No. 10/798,111, Final Office Action dated Jun. 5, 2009.

U.S. Appl. No. 10/798,111, Final Office Action dated Jun. 24, 2008.

U.S. Appl. No. 10/798,111, Final Office Action dated Jan. 12, 2007.

U.S. Appl. No. 10/798,111, Advisory Action dated Nov. 22, 2010.

U.S. Appl. No. 10/798,111, Advisory Office Action dated Sep. 9, 2009.

U.S. Appl. No. 11/441,311, Non-Final Office Action dated Dec. 23, 2010.

U.S. Appl. No. 11/441,311, Non Final Office Action dated Sep. 22, 2009.

U.S. Appl. No. 11/441,311, Final Office Action dated Feb. 19, 2010.

U.S. Appl. No. 11/441,311, Advisory Action dated Jul. 28, 2010.

U.S. Appl. No. 11/755,923, Non-Final Office Action dated Oct. 12, 2010.

U.S. Appl. No. 11/755,923, Non-Final Office Action dated Feb. 22, 2010.

U.S. Appl. No. 11/755,923, Non-Final Office Action dated Mar. 19, 2009.

U.S. Appl. No. 11/755,923, Non-Final Office Action dated Nov. 17, 2008.

U.S. Appl. No. 11/755,923, Non-Final Office Action dated Jun. 24, 2008.

(56) References Cited

OTHER PUBLICATIONS

U.S. Appl. No. 11/755,923, Non-Final Office Action dated Mar. 10, 2008.
U.S. Appl. No. 11/755,923, Non-Final Office Action dated Sep. 7, 2007.
U.S. Appl. No. 11/755,923, Final Office Action dated Oct. 1, 2009.
U.S. Appl. No. 11/755,923, Final Office Action dated Jan. 25, 2008.
U.S. Appl. No. 11/755,923, Advisory Action dated Jan. 25, 2010.
U.S. Appl. No. 11/755,923, Final Office Action dated Apr. 13, 2011.
U.S. Appl. No. 10/798,111, Final Office Action dated Apr. 27, 2011.
U.S. Appl. No. 12/268,301, Non-Final Office Action dated Feb. 1, 2011.
U.S. Appl. No. 11/441,311, Final Office Action dated Apr. 12, 2011.

* cited by examiner

Diffusion Chamber

In-Vitro 24-Hour Biodistribution of Testosterone

In-Vitro Permeation of Testosterone

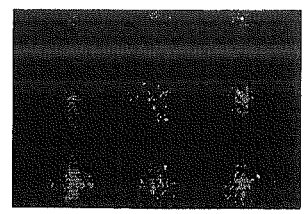
A
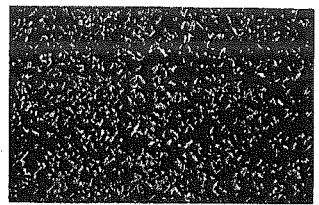
B
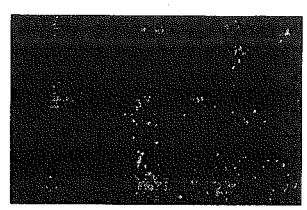
C
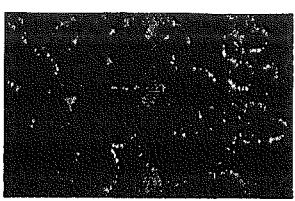
D
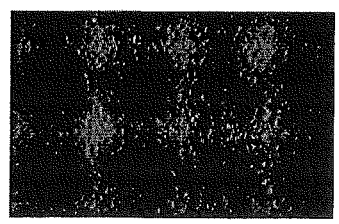
E
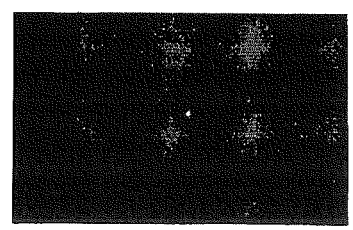
F
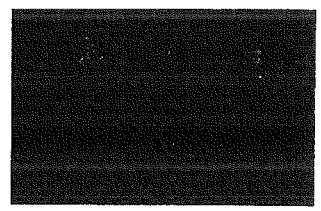
G
H
Figures 5A-5H  Comparative Crystallization Kinetic Studies

TRANSDERMAL TESTOSTERONE FORMULATION FOR MINIMIZING SKIN RESIDUES

CROSS REFERENCE

This application is a continuation of application Ser. No. 12/268,301, filed Nov. 10, 2008 now abandoned, which is a continuation-in-part of application Ser. No. 11/755,923, filed May 31, 2007 now abandoned, which is a continuation-in-part of application Ser. No. 11/371,042, filed Mar. 7, 2006, now U.S. Pat. No. 7,335,379, which is a continuation of International application PCT/EP2004/011175 filed Oct. 6, 2004, which claims the benefit of U.S. Provisional Application No. 60/510,613, filed Oct. 10, 2003. The content of each prior application is expressly incorporated herein by reference.

FIELD OF INVENTION

The present invention relates to a novel transdermal or transmucosal pharmaceutical formulation comprising an active ingredient and a solvent system. The solvent system includes a monoalkyl ether, and glycol in specific ratios, as well as mixture of alcohol and water. The invention also relates to a method of delaying or inhibiting crystallization of an active agent in a transdermal or transmucosal pharmaceutical formulation.

BACKGROUND OF THE INVENTION

It is known that transdermal or transmucosal dosage forms conveniently deliver drugs across a localized area of the skin or the mucosa. One such way of delivering drugs across the skin or mucosa is by way of a non-occlusive transdermal and/or topical dosage form. Some non-limiting examples of non-occlusive transdermal and topical semi-solid dosage forms include creams, ointments, gels, foams, sprays, solutions, and lotions (i.e. emulsions, or suspensions). Typically non-occlusive dosage forms are applied to the skin or mucosa and are left uncovered and open in the atmosphere. Because the non-occlusive dosage form is left uncovered, unwanted transfer of the pharmaceutical formulation to the clothing of the user or even to other individuals in close proximity to the user is unavoidable. Other drawbacks of the non-occlusive dosage form include evaporation of the formulation, removal of the formulation from the skin or mucosa, for example, by bathing or by other activities, and the inabsorption of the formulation through the skin, which is discussed below.

The inefficiencies of drug permeation across or through the skin or mucosa barriers are known. It is also known that the permeation of a drug in a non-occlusive transdermal or transmucosal dosage form can be as little as 1% and usually is no more than 15%. Thus, a vast majority of the active drug remains unabsorbed on the skin or mucosa surface. Because the vast majority of the drug remains on the skin and does not penetrate the skin or mucosa surfaces, the bioavailability of the particular drug is not optimal, and also a high risk of contamination of other individuals in close proximity to the user is presented by the unwanted transfer of the pharmaceutical formulation in the non-occlusive dosage form.

Problems associated with the unwanted transfer of a particular pharmaceutical formulation to others are well documented. For example, Delanoe et al. reported the androgenization of female partners of volunteers applying a testosterone gel preparation during contraceptive studies. (Delanoe, D., Fougeyrollas, B., Meyer, L. & Thonneau, P. (1984): "*Androgenisation of female partners of men on medroxyprogesterone acetate/percutaneous testosterone contraception*", Lancet 1, 276-277). Similarly, Yu et al. reported virilization of a two-year-old boy after incidental and unintentional dermal exposure to a testosterone cream applied to his father's arm and back (Yu, Y. M., Punyasavatsu, N., Elder, D. & D'Ercole, A. J. (1999): "*Sexual development in a two-year old boy induced by topical exposure to testosterone*", Pediatrics, 104, 23).

Moreover, the patient information brochure for ANDROGEL® (1% testosterone gel from Unimed Pharmaceuticals Inc.) emphasizes the potential for transfer of testosterone to other people and/or clothing and the brochure includes safety measures to be taken by the individual using the non-occlusive dosage form.

One way to overcome or minimize this contamination issue is to physically protect the transdermal dosage form by covering skin with the applied pharmaceutical formulation means of a patch device, a fixed reservoir, an application chamber, a tape, a bandage, a sticking plaster, or the like, which remain on the skin at the site of application of the formulation for a prolonged length of time. This is usually accomplished with occlusive dosage forms.

Occlusive dosage forms present some advantages over non-occlusive dosage forms such as assisting the rate of penetration of drugs across the skin by maintaining the thermodynamic activity of the drug close to its maximum (the thermodynamic activity of a drug in a dermal formulation is proportional to the concentration of the drug and the selection of the vehicle, and according to the laws of thermodynamics, the maximum activity of a drug is related to that of the pure drug crystal). However occlusive dosage forms also exhibit several major drawbacks. For example, occlusive dosage forms present a high potential of local skin irritation caused by the prolonged contact on the skin of the drug, volatiles, vehicle excipients, and the adhesive used to attach the occlusive device, e.g., the patch, to the skin. In addition, the occlusive nature of certain occlusive dosage forms, such as the patch device, also restrict the natural ability of the skin to "breathe," and thereby increases the risk of irritation.

In addition to the aforementioned drawbacks of occlusive dosage forms, significant serious hazards have been documented regarding the high drug loading that is specific to patches. For example, several cases of abuses with remaining fentanyl in fentanyl patches have been reported. See, Marquardt K. A., Tharratt R. S., "Inhalation abuse of fentanyl patch.", J Toxicol Clin. Toxicol. 1994; 32(1):75-8; Marquardt K. A., Tharratt R. S., Musallam N. A., "Fentanyl remaining in a transdermal system following three days of continuous use.", Arm Pharmacother. 1995 October; 29(10):969-71; Flannagan L M, Butts J D, Anderson W H., "Fentanyl patches left on dead bodies—potential source of drug for abusers.", J Forensic Sci. 1996 March; 41(2):320-1. Severe incidental intoxication cases have also been documented. See Hardwick Jr., W, King, W., Palmisano, P., "Respiratory Depression in a Child Unintentionally Exposed to Transdermal Fentanyl Patch", Southern Medical Journal, September 1997.

Patch products typically contain patient information, which clearly indicate the risks discussed above. For instance, OXYTROL™ (an oxybutynin patch commercialized by WATSON Pharmaceuticals, Inc. USA) contains patient information that indicates the following warning: "Since the patch will still contain some oxybutynin, throw it away so that it can not be accidentally worn or swallowed by another person, especially a child." The high level of active drug residues is thus a critical drawback of patches. Such accidents could not occur with the use of gel formulations.

Although attempts have been made to overcome drawbacks associated with both occlusive and non-occlusive drug forms, such attempts have been futile. For example, as noted above, one drawback of non-occlusive dosage forms is evaporation of the formulation, which is left open in the atmosphere. The formulation of non-occlusive supersaturated systems could have achieved an ideal merge but transdermal formulations, which rely on supersaturation technologies, present a major drawback of formulation instability, both prior to and during application to the skin due to solvent evaporation. Davis A F and Hadgraft J—Supersaturated solutions as topical drug delivery systems, Pharmaceutical Skin Penetration Enhancement, Marcel Dekker Inc, New York (1993) 243-267 ISBN 0 8247 9017 0, which is incorporated herein by reference.

Notably, extraordinary physicochemical changes occur with the evaporation of the solvent system, which result in modifications of the concentration of the active agent, which may even lead to drug precipitation, thereby altering the diffusional driving force of the formulation. See Ma et al, Proceed. Intern. Symp. Control. Rel. Bioact. Mater., 22 (1995). Consequently, the percutaneous absorption of the active agent may be quite different from that when the solvent was present.

In addition, controlling drug crystallization is of particular interest for non-occlusive transdermal systems. Campbell et al. resorted to a method of heating a crystalline hydrate to a temperature above the melting point in order to prevent the crystallization of the formulation. See, U.S. Pat. No. 4,832,953. Ma et al found that PVP added to the matrix acts as an effective crystallization inhibitor for norethindrone acetate transdermal delivery systems. See, Int. J. of Pharm. 142 (1996) pp. 115-119). DE-A-4210711 affirms that cholesterol and $SiO_2$ are crystallization inhibitors for 17-.beta.-estradiol transdermal delivery system. WO 95/18603 describes soluble PVP as crystal inhibitor for patch devices and affirms that soluble PVP increases the solubility of a drug without negatively affecting the adhesivity or the rate of drug delivery from the pressure-sensitive adhesive composition.

Additionally, the inhibition of crystallization in transdermal devices was reported by Biali et al. See, U.S. Pat. No. 6,465,005 in which it is described that the use of a steroid (estradiol for instance) as an additive in a process of manufacture or storage of a transdermal device acts as a crystallization inhibitor during storage of the device.

Further, transdermal delivery from semi-solid formulations faces antinomic requirements. The drug delivery system should enable absorption of an extensive amount of active drug through the skin within the shortest period of time in order to prevent contamination of individuals, transfer to clothing or accidental removing. The drug delivery system should also provide sustained release of the active drug over 24 hours ideally, so that only once-daily application is required. This drug delivery system should also prevent drug crystallization at the application surface area.

Drug delivery systems having such properties may be achieved by combining various solvents. A volatile solvent may be defined as a solvent that changes readily from solid or liquid to a vapor, that evaporates readily at normal temperatures and pressures. Here below is presented data for some usual solvents, where volatility is reflected by the molar enthalpy of vaporization $\Delta_{vap}H$, defined as the enthalpy change in the conversion of one mole of liquid to gas at constant temperature. Values are given, when available, both at the normal boiling point $t_b$, referred to a pressure of 101.325 kPa (760 mmHg), and at 25° C. (From "Handbook of Chemistry and Physics, David R. Lide, $79^{th}$ edition (1998-1999)—Enthalpy of vaporization (6-100 to 6-115). Stanislaus et al. (U.S. Pat. No. 4,704,406 on Oct. 9, 2001) defined as volatile solvent a solvent whose vapor pressure is above 35 mm Mg when the skin temperature is 32° C., and as non-volatile solvent a solvent whose vapor pressure is below 10 mm Mg at 32° C. skin temperature. Examples of non-volatile solvents include, but are not limited to, propylene glycol, glycerin, liquid polyethylene glycols, or polyoxyalkylene glycols. Examples of volatile solvents include, but are not limited to, ethanol, propanol, or isopropanol.

TABLE 1

Enthalpy of vaporization of certain solvents

| | $t_b$ | $\Delta_{vap}H(t_b)$ | $\Delta_{vap}H(25°C.)$ |
|---|---|---|---|
| Ethanol | 78.3 | 38.6 | 42.3 |
| Propan-2-ol (isopropanol) | 82.3 | 39.9 | 45.4 |
| Propanol | 97.2 | 41.4 | 47.5 |
| Butan-2-ol | 99.5 | 40.8 | 49.7 |
| Butan-1-ol | 117.7 | 43.3 | 52.4 |
| Ethylene glycol monomethyl ether | 124.1 | 37.5 | 45.2 |
| Ethylene glycol monoethyl ether | 135.0 | 39.2 | 48.2 |
| Ethylene glycol monopropyl ether | 149.8 | 41.4 | 52.1 |
| 1,2-Propylene glycol | 187.6 | 52.4 | Not available |
| Diethylene glycol monomethyl ether | 193.0 | 46.6 | Not available |
| Diethylene glycol monoethyl ether | 196.0 | 47.5 | Not available |
| 1,3-Propylene glycol | 214.4 | 57.9 | Not available |
| Glycerin | 290.0 | 61.0 | Not available |

Numerous authors have investigated evaporation and transdermal penetration from solvent systems. For Example, Spencer et al. (Thomas S. Spencer, "*Effect of volatile penetrants on in vitro skin permeability*", AAPS workshop held in Washington D.C. on Oct. 31-Nov. 1, 1986) established that the relationship between volatility and penetration is not absolute and depends on many parameters such as for instance hydration of the tissue or the solubility of the penetrant in the tissue. Stinchcomb et al. reported that the initial uptake of a chemical (hydrocortisone, flurbiprofen) from a volatile solvent system (acetone) is more rapid than that from a non-volatile solvent system (aqueous solution). With an aqueous solution, close to the saturation solubility of the chemical, the driving force for uptake remains more or less constant throughout the exposure period. Conversely, for a volatile vehicle which begins evaporating from the moment of application, the surface concentration of the chemical increases with time up to the point at which the solvent has disappeared; one is now left with a solid film of the chemical from which continued uptake into the stratum corneum may be very slow and dissolution-limited.

Risk assessment following dermal exposure to volatile vehicles should pay particular attention, therefore, to the duration of contact between the evaporating solvent and the skin (Audra L. Stinchcomb, Fabrice Pirot, Gilles D. Touraille, Annette L. Bunge, and Richard H. Guy, "*Chemical uptake into human stratum corneum in vivo from volatile and non-volatile solvents*", Pharmaceutical Research, Vol. 16, No 8, 1999). Kondo et al. studied bioavailability of percutaneous nifedipine in rats from binary (acetone and propylene glycol PG or isopropyl myristate IPM) or ternary (acetone-PG-IPM) solvent systems, compared with the results from simple PG or IPM solvent systems saturated with the drug. (Kondo et al. S, Yamanaka C, Sugimoto I., "*Enhancement of transdermal delivery by superfluous thermodynamic potential. III Percutaneous absorption of nifedipine in rats*", J Pharmaco Biodyn. 1987 December; 10(12):743-9).

U.S. Pat. No. 6,299,900 to Reed et al. discloses a non-occlusive, percutaneous, or transdermal drug delivery system-having active agent, safe and approved sunscreen as penetration enhancer, and optional volatile liquid. The invention describes a transdermal drug delivery system, which comprises at least one physiologically active agent or prodrug thereof and at least one penetration enhancer of low toxicity being a safe skin-tolerant ester sunscreen. The composition comprises an effective amount of at least one physiologically active agent, at least one non-volatile dermal penetration enhancer; and at least one volatile liquid.

U.S. Pat. No. 5,891,462 to Carrara discloses a pharmaceutical formulation in the form of a gel suitable for the transdermal administration of an active agent of the class of estrogens or of progestin class or of a mixture of both, comprising lauryl alcohol, diethylene glycol monoethyl ether and propylene glycol as permeation enhancers.

Mura et al. describe the combination of diethylene glycol monoethyl ether and propylene glycol as a transdermal permeation enhancer composition for clonazepam (Mura P., Faucci M. T., Bramanti G., Corti P., "Evaluation of transcutol as a clonazepam transdermal permeation enhancer from hydrophilic gel formulations", Eur. J. Pharm. Sci., 2000 February; 9(4): 365-72)

Williams et al. reports the effects of diethylene glycol monoethyl ether (TRANSCUTOL™) in binary co-solvent systems with water on the permeation of a model lipophilic drug across human epidermal and silastic membranes (A. C. Williams, N. A. Megrab and B. W. Barry, "*Permeation of oestradiol through human epidermal and silastic membranes from saturated TRANSCUTOL®/water systems*", in Prediction of Percutaneous Penetration, Vol. 4B, 1996). Many references may also illustrate the effect of TRANSCUTOL™ as an intracutaneous drug depot builder well known to one skilled in the art.

U.S. Pat. No. 5,658,587 to Santus et al. discloses transdermal therapeutic systems for the delivery of alpha adrenoceptor blocking agents using a solvent enhancer system comprising diethylene glycol monoethyl ether and propylene glycol.

U.S. Pat. No. 5,662,890 to Punto et al. discloses an alcohol-free cosmetic compositions for artificially tanning the skin containing a combination of diethylene glycol monoethyl ether and dimethyl isosorbide as permeation enhancer.

U.S. Pat. No. 5,932,243 to Fricker et al. discloses a pharmaceutical emulsion or microemulsion preconcentrate for oral administration of macrolide containing a hydrophilic carrier medium consisting of diethylene glycol monoethyl ether, glycofurol, 1,2-propylene glycol, or mixtures thereof.

U.S. Pat. Nos. 6,267,985 and 6,383,471 to Chen et al. disclose pharmaceutical compositions and methods for improved solubilization of triglycerides and improved delivery of therapeutic agents containing diethylene glycol monoethyl ether and propylene glycol as solubilizers of ionizable hydrophobic therapeutic agents.

U.S. Pat. No. 6,426,078 to Bauer et al. discloses an oil-in water microemulsion containing diethylene glycol monoethyl ether or propylene glycol as co-emulsifier of lipophilic vitamins.

Many research experiments have been carried out on diethylene glycol monoethyl ether (marketed under the trademark TRANSCUTOL™ by Gattefossé) as an intracutaneous drug depot builder. For example, Ritschel, W. A., Panchagnula, R., Stemmer, K., Ashraf, M., "*Development of an intracutaneous depot for drugs. Binding, drug accumulation and retention studies, and mechanism depot for drugs*", Skin Pharmacol, 1991; 4: 235-245; Panchagnula, R. and Ritschel, W. A., "*Development and evaluation of an intracutaneous depot formulation of corticosteroids using TRANSCUTOL® as a cosolvent, in vitro, ex vivo and in-vivo rat studies*", J. Pharm. Pharmacology. 1991; 43: 609-614; Yazdanian, M. and Chen, E., "*The effect of diethylene glycol monoethyl ether as a vehicle for topical delivery of ivermectin*", Veternary Research Com. 1995; 19: 309-319; Pavliv, L., Freebern, K., Wilke, T., Chiang, C-C., Shetty, B., Tyle, P., "*Topical formulation development of a novel thymidylate synthase inhibitor for the treatment of psoriasis*", Int. J. Pharm., 1994; 105: 227-233; Ritschel, W. A., Hussain, A. S., "*In vitro skin permeation of griseofulvin in rat and human skin from an ointment dosage form*", Arzneimeittelforsch/Drug Res. 1988; 38: 1630-1632; Touitou, E., Levi-Schaffer, F., Shaco-Ezra, N., Ben-Yossef, R. and Fabin, B., "*Enhanced permeation of theophylline through the skin and its effect on fibroblast proliferation*", Int. J. Pharm., 1991; 70: 159-166; Watkinson, A. C., Hadgraft, J. and Bye, A., "*Enhanced permeation of prostaglandin $E_2$ through human skin in vitro*", Int. j. Pharm., 1991; 74: 229-236; Rojas, J., Falson, F., Courraze, G., Francis, A., and Puisieux, F., "*Optimization of binary and ternary solvent systems in the percutaneous absorption of morphine base*", STP Pharma Sciences, 1991; 1: 71-75; Ritschel, W. A., Barkhaus, J K., "*Use of absorption promoters to increase systemic absorption of coumarin from transdermal drug delivery systems*", Arzneimeittelforsch/Drug Res. 1988; 38: 1774-1777.

U.S. Pat. No. 5,580,574 to Behl et al. discloses a pharmaceutical composition comprising a solvent system made of isopropanol, propylene glycol, oleic acid, water, and optional additional ingredients such as diacetin, caprylic acid, or transcutol. The composition can exist as a gel or as a thickened solution. It is restricted, however, to the transdermal administration of benzodiazepines or benzodiazepine antagonists to a host in need thereof, preferably as a transdermal patch or a reservoir type, i.e., as an occlusive formulation.

Thus, there remains a need to provide a pharmaceutically acceptable transdermal or transmucosal pharmaceutical formulation or drug delivery system that exhibits the advantages of both occlusive systems (high thermodynamic activity) and non-occlusive systems (low irritation and sensitization potential, and excellent skin tolerance) while overcoming the disadvantages of these systems. The novel transdermal or transmucosal pharmaceutical formulation of the present invention satisfies this need.

SUMMARY OF INVENTION

The transdermal or transmucosal pharmaceutical formulation of the present invention comprises at least one active agent, preferably testosterone; and a solvent system present in an amount sufficient to solubilize the at least one active ingredient and inhibit crystallization of the at least one active ingredient on a skin or mucosal surface of a mammal. Other advantages of the transdermal or transmucosal pharmaceutical formulation of the invention include reducing or preventing the transfer of the formulation to clothing or another, minimizing contamination of clothing by the formulation, modulation of biodistribution of the active agent within different layers of the skin and facilitation of absorption of the active agent by the skin or mucosa surface to name a few.

The novel solvent system of the present invention includes a monoalkyl ether, present in an amount of between about 1% and 30% by weight of the solvent system, a glycol, present in an amount of between about 1% and 30% by weight of the solvent system. The monoalkyl ether and glycol are present in a weight ratio of 10:1 to 2:1 or 1:2 to 1:10 and preferably 1:4 to 1:10. The solvent system further includes a mixture of an alcohol and water. The mixture present in an amount of between about 40% and 98% of the solvent system, wherein the alcohol is present in an amount of about 5% to 80% of the mixture, and the water is present in an amount of about 20% to 95% of the mixture.

Surprisingly, it has been discovered that the combinative use of a monoalkyl ether of diethylene glycol and a glycol at specified ratios, preferably in hydro-alcoholic formulations, prevents or significantly reduces the transfer of active drug(s) from transdermal semi-solid formulations to clothing or other surfaces, significantly reduces the transfer to individuals; and also prevents or significantly reduces the loss of active drug (s)—and therefore the loss of therapeutic efficiency—consecutive to accidental removing due to daily activities such as washing, swimming or the like.

Other advantages of the present invention include the discovery that the association of a monoalkyl ether and a glycol at specified ratios exhibit a synergic effect and inhibits crystallization of the active ingredient(s) in transdermal semi-solid formulations. In addition, it has been discovered, against the background described above, a totally unexpected control of the active drug(s) distribution in the different layers of the skin is achieved when modifying the range of the monoalkyl ether:glycol ratio described in the present invention, simultaneously but independently from the crystallization inhibitor effect above mentioned.

Further, it has also been found that the glycol acts as a modulator of the capability of monoalkyl ether to build a drug depot in the different layers of the skin. Also, the significant reduction of unabsorbed active drug(s) remaining at the application surface area results from the simultaneous although independent inhibition of crystallization and transdermal drug penetration, enhanced or not by additional permeation enhancer(s).

BRIEF DESCRIPTION OF THE DRAWINGS

FIGS. 5A to 5H illustrate results of crystallization kinetic studies of prior art compositions compared to formulations in accordance with the present invention.

DETAILED DESCRIPTION OF THE PREFERRED EMBODIMENTS

Figure 1:
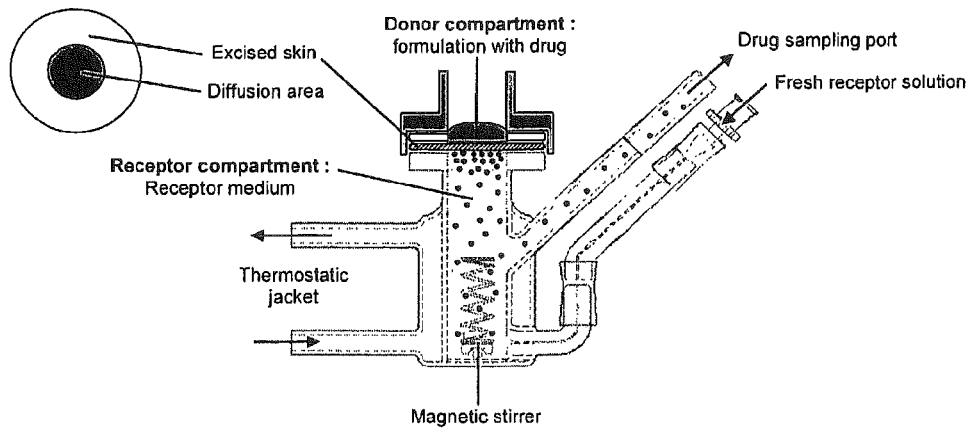
FIG. 1 is schematically illustrates a diffusion chamber used for vertical diffusion cell used for in vitro testing of transdermal formulations.

The present invention is directed to a novel transdermal or transmucosal pharmaceutical formulation. The formulation comprises at least one active ingredient of testosterone and a solvent system that includes:

(i) a pharmaceutically acceptable monoalkyl ether of diethylene glycol present in an amount of between about 1% and 30% by weight of the solvent system;

(ii) a pharmaceutically acceptable glycol present in an amount of between about 1% and 30% by weight of the solvent system, with the monoalkyl ether of diethylene glycol and the glycol being present in a weight ratio of 1:4 to 1:10; and (iii) a mixture of a C2 to C4 alcohol and water which mixture is present in an amount of between about 40% and 98% of the solvent system, wherein the C2 to C4 alcohol is present in an amount of about 5% to 80% of the mixture, and the water is present in an amount of about 20% to 95% of the mixture.

The monoalkyl ether of diethylene glycol and the glycol in combination are present in amount of at least 15% and no more than 60% of the formulation, so that, compared to formulations containing the same components but in different amounts and ratios, the present solvent system (a) inhibits crystallization of the at least one active ingredient on a skin or mucosal surface of a mammal, (b) reduces or prevents transfer of the formulation to clothing or to another being, (c) modulates biodistribution of the at least one active ingredient within different layers of skin, (d) facilitates absorption of the at least one active ingredient by a skin or a mucosal surface of a mammal or (e) provides a combination of one or more of (a) through (d).

In accordance with the present invention, the transdermal or a transmucosal drug delivery formulation is in the form of a semi-solid formulation, gel, a cream, an ointment, a lotion (i.e. an emulsion or a dispersion), a solution, a foam, or a spray although alternatives are also in the scope of the claims.

The phrase "semi-solid" formulation means a heterogeneous system in which one solid phase is dispersed in a second liquid phase.

The phrase "transdermal" delivery, applicants intend to include both transdermal (or "percutaneous") and transmucosal administration, i.e., delivery by passage of a drug through the skin or mucosal tissue and into the bloodstream.

The phrase "pharmacologically active" or "physiologically active" to describe "ingredient" or "agent" as used herein means any chemical material or compound suitable for transdermal or transmucosal administration which induces a desired systemic effect.

The phrase "therapeutically effective" amount of a pharmacologically active agent means a non toxic but sufficient amount of a compound to provide the desired therapeutic effect.

The phrase "non-occlusive" system as used herein means a system that does not trap nor segregate the skin from the atmosphere by means of for instance a patch device, a fixed reservoir, an application chamber, a tape, a bandage, a sticking plaster, or the like which remains on the skin at the site of application for a prolonged period of time.

The phrase "contamination" or "transfer" as used herein means the unintended presence of harmful substances in individuals or surfaces by direct contact between individuals, between surfaces, or between individuals and surfaces (and reciprocally).

The phrase "synergy", "synergism", "synergistic effect" or "synergistic action" as used herein means an effect of the interaction of the actions of two agents such that the result of the combined action is greater than expected as a simple additive combination of the two agents acting separately.

The phrase "modulate", "regulate" or "control" as used herein means to adjust, or maintain, with respect to a desired rate, degree, or condition, as to adjust permeation rate, crystallization speed, repartition of an active pharmaceutical ingredient in the layers of the skin.

The phrase "effective" or "adequate" permeation enhancer or combination as used herein means a permeation enhancer or a combination that will provide the desired increase in skin permeability and correspondingly, the desired depth of penetration, rate of administration, and amount of drug delivered.

The phrase "monoalkylether of diethylene glycol" means a chemical having general formula $C_4H_{10}O_3(C_nH_{2n+1})$ wherein n=1-4. Further, the term "glycol" encompasses a broad range of chemicals including but not limited to propylene glycol, dipropylene glycol, butylene glycol, and polyethyleneglycols having general formula HOCH$_2$(CH$_2$OH)$_n$CH2OH wherein n (number of oxyethylene groups)=4-200.

The phrase "thermodynamic activity" of a substance means the energy form involved in skin permeation of this substance. The chemical potential of a substance is defined in thermodynamics as the partial molar free energy of the substance. The difference between the chemical potentials of a drug outside and inside the skin is the energy source for the skin permeation process.

The phrase "permeation enhancer" as used herein means an agent which improves the rate of percutaneous transport of active agents across the skin or use and delivery of active agents to organisms such as animals, whether for local application or systemic delivery.

The phrase "stratum corneum" as used herein means the outer layer of the skin, which comprised approximately 15 layers of terminally differentiated keratinocytes made primarily of the proteinaceous material keratin arranged in a 'brick and mortar' fashion with the mortar being comprised of a lipid matrix made primarily from cholesterol, ceramides and long chain fatty acids. The stratum corneum creates the rate-limiting barrier for diffusion of the active agent across the skin.

The phrase "skin-depot" as used herein means a reservoir or deposit of active agent and dermal penetration enhancer within the stratum corneum, whether it is intra-cellular (within keratinocytes) or inter-cellular.

As stated above, the present invention relates to a transdermal or a transmucosal drug delivery formulation. The invention relates more specifically to a non-occlusive transdermal or transmucosal formulation, preferably in the form of a gel, for use in the delivery of at least one pharmaceutical active ingredient to a warm-blooded animal. Formulations of the present invention may be used for local or systemic delivery.

The formulation may include a permeation enhancer, gelling agent, preservative, antioxidant, buffer, humectant, sequestering agent, moisturizer, surfactant, emollient, or any combination thereof.

In one embodiment, the pharmaceutical formulation includes testosterone as an active agent and the monoalkyl ether of diethylene glycol and the glycol are in a weight ratio of 1:4 to 1:10.

In another aspect of the invention, a method for delaying or inhibiting crystallization of an active agent in a transdermal or transmucosal formulation is provided. It has surprisingly been found that the present invention inhibits or delays for a significant period of time crystallization of the active agent on the skin or mucosal surface. One problem associated with crystallization of the drug on the skin is that the crystals have difficulty crossing the skin or mucosal barrier. Thus, the active agent is left on the skin surface for an extended period of time. As such, there is an increase in the likelihood that the active agent is transferred to clothing or contaminates another being that comes in contact with the user of the pharmaceutical formulation. The present invention by inhibiting or delaying crystallization of the active agent has at least three advantage. The delay or inhibition of the active agent will increase absorption of the drug across the skin or mucosal barrier. Accordingly, there is a minimization of transfer of the pharmaceutical formulation to clothing. Moreover, there is a minimization of contamination of active agent to others.

In accordance with the present invention, the transdermal or a transmucosal pharmaceutical formulation is a drug delivery formulation comprising an active ingredient and a solvent system. The solvent system of the invention includes a pharmaceutically acceptable monoalkyl ether, a pharmaceutically acceptable glycol, and a mixture of an alcohol and water.

For example, the monoalkyl ether is diethylene glycol monomethyl ether, diethylene glycol monoethyl ether or mixtures thereof. Also for example the glycol is propylene glycol, dipropylene glycol or mixtures thereof. The monoalkyl ether and glycol are present in an amount between about 1% and 30% w/w each, and are present in a ratio ranging from 10:1 to 2:1 or 1:2 to 1:10 and preferably 1:4 to 1:10. In a preferred embodiment the pharmaceutically acceptable monoalkyl ether is diethylene glycol monoethyl ether and the glycol is propylene glycol.

Preferably, the solvent system includes a combination of volatile and non-volatile solvents. Examples of non-volatile solvents include but are not limited to propylene glycol, glycerin, liquid polyethylene glycols, or polyoxyalkylene glycols. Examples of volatile solvents include but are not limited to ethanol, propanol, or isopropanol. Preferably, the volatile solvent is a $C_2$-$C_4$ alcohol. For example, the $C_2$-$C_4$ alcohol is preferably ethanol, isopropanol, or mixtures of thereof. The $C_2$-$C_4$ alcohol is present in an amount between about 5 and 80% w/w, and preferably between 15 and 65%, and more preferably between 20 and 50%.

It is to be understood that the "active agent" is intended to mean a single active agent or a combination of more than one active agent. The amount of the systemically and/or topically active agent included in the formulation is subject to the degree to which penetration enhancement is achieved.

Also in accordance with the invention, permeation enhancers may be additionally incorporated to the pharmaceutical formulation. Permeation enhancers include but are not limited to sulfoxides such as dimethylsulfoxide and decylmethylsulfoxide; surfactants such as sodium laurate, sodium lauryl sulfate, cetyltrimethylammonium bromide, benzalkonium chloride, poloxamer (231, 182, 184), tween (20, 40, 60, 80) and lecithin; the 1-substituted azacycloheptan-2-ones, particularly 1-n-dodecylcyclazacycloheptan-2-one; fatty alcohols such as lauryl alcohol, myristyl alcohol, oleyl alcohol and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate, amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine, terpenes; alkanones, and organic acids, particularly salicylic acid and salicylates, citric acid and succinic acid. As noted earlier herein, "Percutaneous Penetration Enhancers", eds. Smith et al. (CRC Press, 1995), which is incorporated herein by reference thereto, provides an excellent overview of the field and further information concerning possible secondary enhancers for use in conjunction with the present invention. More permeation enhancer(s) suitable to be used with the present invention may be known by those skilled in the art. The permeation enhancer is present from about 0.1 to about 30.0% w/w depending on the type of compound. Preferably the permeation enhancers are fatty alcohols and fatty acids, and more preferably fatty alcohols. Preferably, the fatty alcohols have the formula the CH3(CH2)n(CH)mCH2OH wherein n ranges from (8-m) to (16-m) and m=0-2.

The pharmaceutical formulation of the invention may further include a gelling agent or thickener, e.g. carbomer, carboxyethylene or polyacrylic acid such as carbomer 980 or 940 NF, 981 or 941 NF, 1382 or 1342 NF, 5984 or 934 NF, ETD 2020, 2050, 934P NF, 971P NF, 974P NF and carbomer derivatives; cellulose derivatives such as ethylcellulose, hydroxypropylmethylcellulose (HPMC), ethyl-hydroxyethylcellulose (EHEC), carboxymethylcellulose (CMC), hydroxypropylcellulose (HPC), hydroxyethylcellulose (HEC), etc; natural gums such as arabic, xanthan, guar gums, alginates, etc; polyvinylpyrrolidone derivatives; polyoxyethylene polyoxypropylene copolymers, etc; others like chitosan, polyvinyl alcohols, pectins, veegum grades, and the like. Other suitable gelling agents to apply the present invention include, but are not limited to, carbomers. Alternatively, other gelling agents or viscosant known by those skilled in the art may also be used. The gelling agent or thickener is present from about 0.2 to about 30% w/w depending on the type of polymer, as known by one skilled in the art.

The transdermal or transmucosal pharmaceutical formulation may further include preservatives such as benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative is present from about 0.01 to about 10% w/w depending on the type of compound.

The transdermal or transmucosal pharmaceutical formulation may further comprise an antioxidant such as but not limited to tocopherol and derivatives, ascorbic acid and derivatives, butylated hydroxyanisole, butylated hydroxytoluene, fumaric acid, malic acid, propyl gallate, metabisulfates and derivatives. The antioxidant is present from about 0.001 to about 5.0 w/w depending on the type of compound.

Also in accordance with the invention, the formulation may further comprise buffers such as carbonate buffers, citrate buffers, phosphate buffers, acetate buffers, hydrochloric acid, lactic acid, tartaric acid, diethylamine, triethylamine, diisopropylamine, aminomethylamine. Although other buffers as known in the art may be included. The buffer may replace up to 100% of the water amount within the formulation.

In one embodiment, the transdermal or transmucosal pharmaceutical formulation further comprises humectant such as glycerin, propylene, glycol, sorbitol, triacetin. The humectant is present from about 1 to 10% w/w depending on the type of compound.

The present formulation may further comprise sequestering agent such as edetic acid. The sequestering agent is present from about 0.001 to about 5% w/w depending on the type of compound.

Also in accordance with the invention, the formulation includes a moisturizer such as docusate sodium, polyoxyethylene alkyl ethers, polyoxyethylene castor oil derivatives, polyoxyethylene stearates, polyoxyethylene sorbitan fatty acid esters, sodium lauryl sulfate. The moisturizer is present from about 1.0 to about 5 w/w depending on the type of compound.

The formulation may further comprise anionic, nonionic, or cationic surfactants. The surfactant is present from about 0.1 to about 30% w/w depending on the type of compound.

Also in accordance with the present invention, the formulation comprises emollients such as but not limited to cetostearyl alcohol, cetyl esters wax, cholesterol, glycerin, fatty esters of glycerol, isopropyl myristate, isopropyl palmitate, lecithins, light mineral oil, mineral oil, petrolatum, lanolins, and combinations thereof. The emollient is present from about 1.0 to about 30.0% w/w depending on the type of compound.

In another aspect of the present invention a method is provide for delaying or inhibiting crystallization of an active agent in a transdermal or transmucosal pharmaceutical formulation. The method includes preparing a formulation comprising at least one active agent and a solvent system, which includes a pharmaceutically acceptable monoalkyl ether of diethylene glycol and a glycol present in a weight ratio of 10:1 to 2:1 or 1:2 to 1:10. In a preferred embodiment of the method, the monoalkyl ether of diethylene glycol and the glycol are present in an amount of about 1:4 to 1:10.

Preferably, the monoalkyl ether of diethylene glycol and the glycol in combination are present in an amount of at least 15% and no more than 60% of the formulation.

Advantageously, the method decreases or inhibits crystallization of the active agent such that absorption and permeation through the skin or mucosal surface to which it is applied is facilitated or increased. Preferably, the formulation includes a permeation enhancer to increase permeability of the active agent across a dermal or mucosal surface. For example, the formulation may further include lauryl alcohol or myristyl alcohol in an amount between 0.5 to 2% by weight of the total formulation.

EXAMPLES

The following examples are illustrative, and should not be interpreted as limitations to the invention.

Example 1

A gel containing testosterone 1.00% weight by weight (w/w), diethylene glycol monoethyl ether 5.00% w/w, propylene glycol 6.00% w/w, ethanol 46.28% w/w, purified water 38.11% w/w, carbomer (CARBOPOL™ 980 NF) 1.20% w/w, triethanolamine 0.35% w/w, disodium edetic acid (EDTA) 0.06% w/w, lauryl alcohol 2.00% w/w was prepared by dissolving the active ingredient (if not hydrosoluble) in the ethanol/propylene glycol/diethylene glycol monoethyl ether/lauryl alcohol mixture. The disodium EDTA solution was then added and carbomer thoroughly dispersed in the hydroalcoholic solution under mechanical stirring at room temperature at a suitable speed ensuring good homogenization of the formulation while avoiding lumps formation and air entrapment. Triethanolamine was finally added under stirring to form the gel.

Example 2

A gel composed by testosterone 1.00% w/w, diethylene glycol monoethyl ether 5.00% w/w, propylene glycol 30.0% w/w, ethanol 34.31% w/w, purified water 28.07% w/w, carbomer (CARBOPOL™ 980 NF) 1.20% w/w, triethanolamine 0.35% w/w, disodium EDTA 0.06% w/w, was prepared according to the manufacturing technique described in Example 1.

Example 3

A gel composed by testosterone 1.00% w/w, estradiol 0.10% w/w, diethylene glycol monoethyl ether (TRANSCUTOL™ P) 5.00 w/w, propylene glycol 30.0% w/w ethanol 38.00% w/w, purified water 25.40% w/w, hydroxypropylcellulose (KLUCEL™ MF Pharm) 0.50% w/w, was prepared by dissolving the active ingredient (if not hydrosoluble) in the ethanol/propylene glycol/diethylene glycol monoethyl ether/lauryl alcohol mixture. Purified water was then added and hydroxypropylcellulose thoroughly dispersed in the hydroalcoholic solution under mechanical stirring at room temperature at a suitable speed ensuring good homogenization of the formulation while avoiding lumps formation and air entrapment until complete swelling.

Comparative Examples of—In Vitro Drug Biodistribution and Permeation Studies

Example 4

In vitro drug biodistribution and permeation experiments through ear pig skin were made using the diffusion chamber that is schematically shown in FIG. 1 (Franz Vertical Diffusion Cell). Cutaneous penetration studies in vitro through human skin are limited due to the lack of availability of the human skin. It is largely described in the literature that ear pig skin can be used as the closest model to human skin in the assessment of percutaneous absorption of chemicals.

Fresh cadaver ear pig skin obtained from slaughterhouses was processed according to standard operating procedures. The ears were evaluated on their integrity (no bites, scratches or redness) and condition. The skin was excised from the ears with the help of scalpels, avoiding perforations or any damage. The excised skin samples were rinsed with PBS solution and placed on a surface for successive punching of skin disks. The skin disk pieces were mounted between the sections of a vertical diffusion cell having 1.77 sqcm of surface area, the epidermal facing up. 50 mg of the transdermal devices exemplified previously was applied over the epidermal layer whilst the dermal layer contact with the receptor solution: 2.0% weight by volume polyoxyethylene 20 oleyl ether (Oleth 20), with phosphate buffer solution PBS 10 mM, pH 7.4. The receptor chamber was maintained at 35° C. and the studies were conducted under non-occlusive conditions and at 600 rpm of stirring speed. At given time points, samples were withdrawn from the receptor solution and the receptor chamber was immediately refilled with fresh solution. All samples taken from the receptor solution (permeated drug) were analyzed using a high performance liquid chromatography (HPLC) method. After completion of the permeation study, and utilizing appropriate solvents formulation, all skin disk pieces were analysed in drug distribution within the skin layers: dermis, epidermis and stratum corneum. Unabsorbed formulation was also assessed. Then, balance mass was performed in order to assess total recovery/distribution of drug after certain time following drug product administration/application, considering unabsorbed formulation, the amount of drug in the stratum corneum and the amount of drug within the innermost layers of the skin (epidermis, dermis, and receptor solution representing the bloodstream). The different compartments were analyzed using a high performance liquid chromatography (HPLC) method.

Cumulated Drug Permeated and Drug Flux Determination (In Vitro Permeation Study)

The total amount of drug permeated (mcg/cm2) during the study duration and the transdermal flux (mcg/sqcm/h) were determined for each study.

Biodistribution Study

After completion of the in vitro permeation study, distribution of the active compound was assessed for the different compartments as explained before. In order to demonstrate the improvements in the permeation performance applying the invention herein discloses, as well as improvements in minimizing amount of drug that can potentially being transferred to clothes or partners, in vitro permeation studies and drug biodistribution studies of examples using the inventive means were compared with examples made without using this invention. It was an objective to demonstrate the results obtained applying the invention herein disclose. By carrying out drug biodistribution studies in vitro and though, assessing the amount of drug remaining on the skin surface which can potentially be transmitted or transferred to other surfaces or partners when the formulation is used "in vivo".

Example 5

Comparison Between a Formulation of the Present Invention and a Prior Art Formulation Refer to "Examples" above for the quali-quantitative formulations of the examples cited below.

Testosterone 24-Hour Biodistribution

Normalized Recovery (% of Total Relative Recovery)

TABLE I

Testosterone in vitro 24-hour biodistribution

| Compartments | Control | | | Example 2 (TC:PG ratio 1:6) | | | Comparative Formulation (TC:PG ratio 5:1) | | |
|---|---|---|---|---|---|---|---|---|---|
| | Mean % | SD % | N | Mean % | SD % | N | Mean % | SD % | N |
| Unabsorbed formulation | 92.5 | 20.1 | 4 | 66.5 | 32.2 | 4 | 82.4 | 15.9 | 4 |
| Stratum corneum | 5.7 | 3.0 | 4 | 12.6 | 8.3 | 4 | 6.6 | 4.0 | 4 |
| Epidermis | 1.8 | 0.5 | 4 | 20.9 | 4.8 | 4 | 11.1 | 5.5 | 4 |
| Dermis | | | | | | | | | |
| Receptor | | | | | | | | | |
| TOTAL | 100.0 | | | 100.0 | | | 100.0 | | |

Figure 2:
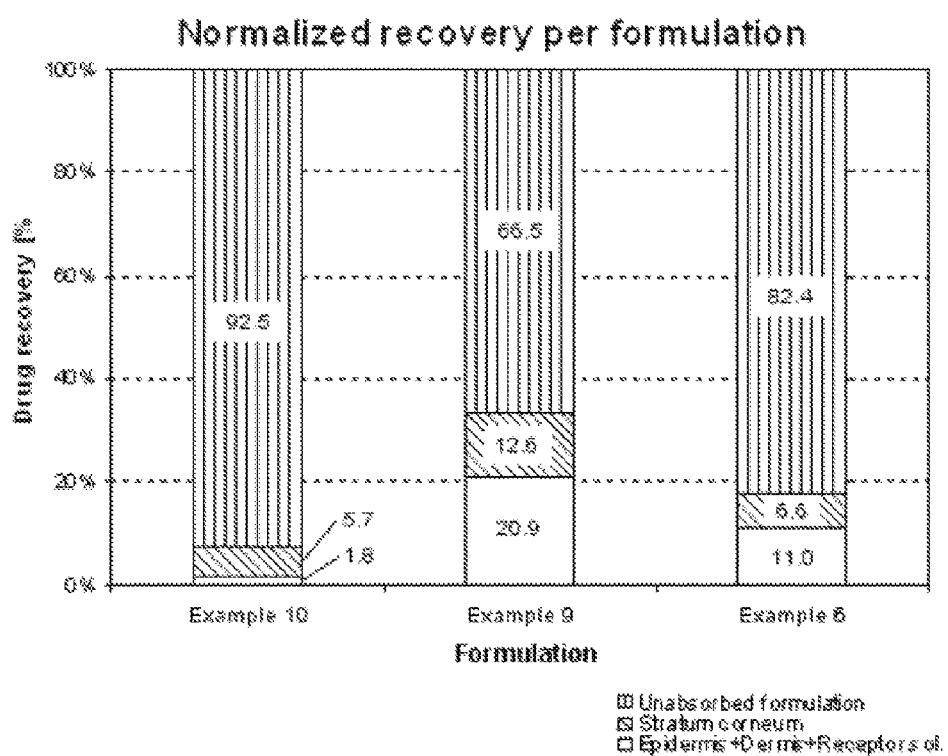
FIG. 2 is a graph illustrating in-vitro 24-hour biodistribution of Testosterone of selected formulation examples disclosed herein.

Table 1 above clearly shows a significant decrease in the amount of drug that is unabsorbed when a transdermal or transmucosal formulation of the present invention is used compared a transdermal or transmucosal formulation that does not include the novel ratio of monoalkyl ester and glycol. As shown, after 24 h, a huge amount of testosterone (92.5%) remained unabsorbed from the Control formulation, which does not include the novelty of the present invention, conversely, examples 2 had significantly less unabsorbed drug, 66.5%. FIG. 2 illustrates these results in graphic format.

Table 1 above and FIG. 2 show that a higher amount of testosterone (12.6% versus 6.6%) is present in the stratum corneum in example 9 where the invention is present in a ratio of 1:6. This result shows that accumulation of active drug in the outermost layer of the skin or the mucosa does result from the combination of diethylene glycol monoethyl ether:propylene glycol in defined ratios, and does not only depend on diethylene glycol monoethyl ether concentration as expected by the background described previously.

This biodistribution study demonstrates the usefulness of the present invention (i.e. a combination of diethylene glycol monoethyl ether and propylene glycol tested in this case at two extreme ratios: 1:6 and 5:1) and that the present invention significantly reduces formulation skin residues.

Example 6

Comparison Between Formulation Containing the Invention Herein Described in Different Ratios Three different formulations, each of which contained a fixed concentration of diethylene glycol monoethyl ether (5% w/w) and a variable concentration of propylene glycol (6, 15 or 30% w/w) were prepared, and compared in a drug permeation and a drug biodistribution after 24 hours between the Control and Examples 1 and 2 above. The results of the permeation study are found in Table II below.

Testosterone 24-Hour In Vitro Permeation

TABLE II

Testosterone 24-hour in vitro permeation

Testosterone Cumulative Amount - 24 hours ($\mu g/cm^2$)
Mean ± SD

| Time (h) | Control | Example 1 | Example 2 |
|---|---|---|---|
| 0 | 0 | 0 | 0 |
| 6 | 3.9 ± 3.1 | 2.1 ± 1.7 | 1.5 ± 1.0 |
| 12 | 10.9 ± 6.1 | 9.9 ± 8.3 | 7.2 ± 5.6 |
| 18 | 16.9 ± 6.5 | 21.4 ± 13.4 | 18.1 ± 12.0 |
| 24 | 20.7 ± 6.7 | 31.0 ± 14.5 | 29.5 ± 14.6 |

Figure 3:
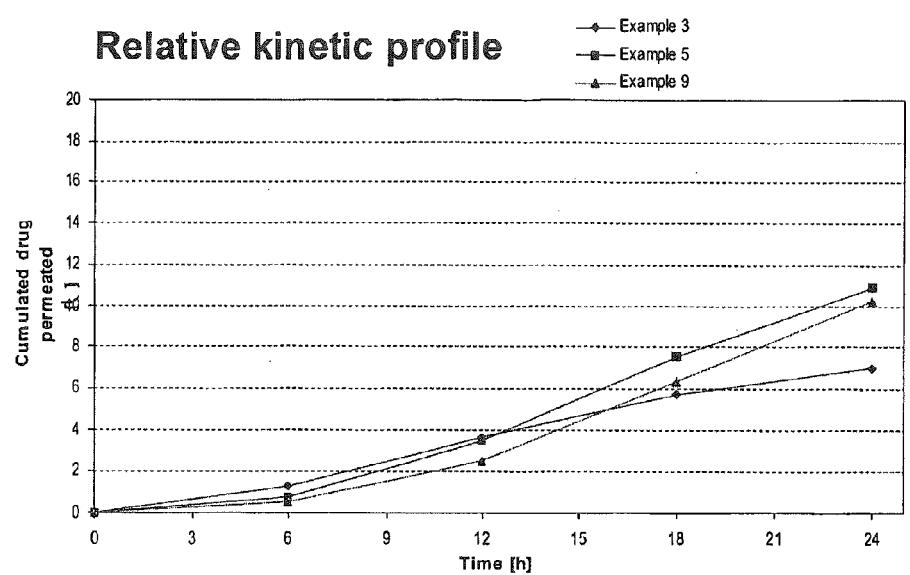
FIG. 3 is a kinetic profile of in-vitro permeation of Testosterone of selected formulation examples disclosed herein.

Table II shows that three different formulations, each of which have different ratios ranging from 1:1.2 to 1:6 of diethylene glycol monoethyl ether:propylene glycol, result in significantly similar cumulated amounts of permeated testosterone. FIG. 3 illustrates the relative kinetic profile of each of these three formulations.

Changes in the quantitative formulation of the present invention do not result in any significant permeation variation.

Testosterone 24-Hour Biodistribution

Normalized Recovery (% of Total Relative Recovery)

TABLE III

Testosterone 24-hour biodistribution

| Compartments | Control | | | Example 2 (TC:PG ratio 1:6) | | | Comparative Formulation (TC:PG ratio 5:1) | | |
|---|---|---|---|---|---|---|---|---|---|
| | Mean % | SD % | N | Mean % | SD % | N | Mean % | SD % | N |
| Unabsorbed formulation | 88.6 | 4.1 | 4 | 79.0 | 18.5 | 4 | 75.1 | 16.0 | 4 |
| Stratum corneum | 2.6 | 1.5 | 4 | 4.8 | 2.2 | 4 | 8.1 | 3.1 | 4 |
| Epidermis | 8.8 | 2.3 | 4 | 16.2 | 4.8 | 4 | 16.8 | 3.5 | 4 |
| Dermis | | | | | | | | | |
| Receptor | | | | | | | | | |
| TOTAL | 100.0 | | | 100.0 | | | 100.0 | | |

Figure 4:
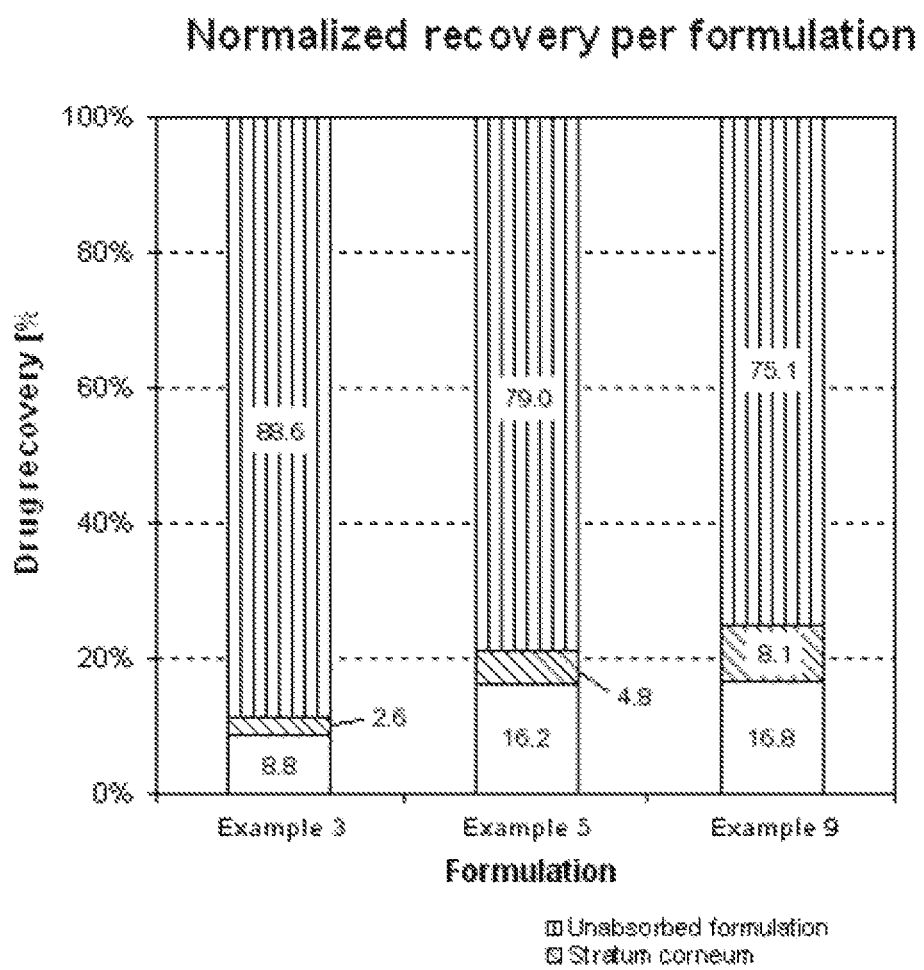
FIG. 4 is a graph illustrating in vitro 24 hour biodistribution of Testosterone of the formulation examples shown in FIG. 3.

As shown in Table III above, and in FIG. 4, increasing the ratio of the present formulation from 1:3 (5% w/w diethylene glycol monoethyl ether/15% w/w propylene glycol) to 1:6 in example 2 (5% w/w diethylene glycol monoethyl ether/30% w/w propylene glycol) only resulted in a 5% decrease of unabsorbed drug, but resulted in a about 66% increase of drug distributed in the stratum corneum. Drug distributed deeper in the skin layers can be considered as unchanged. This study demonstrates that it is possible to modify the distribution of the active drug within the outermost layers of the skin or the mucosa while simultaneously not affecting significantly drug distribution in the innermost layers of the skin or the mucosa.

This set of in vitro permeation and biodistribution studies clearly demonstrate that drug distribution is modulated by the ratio of the formulation. These in vitro permeation and biodistribution studies also clearly demonstrate that changes of the ratio in which the novel formulation do not result in significantly different permeation performances. Additionally, these in vitro permeation and biodistribution studies clearly demonstrate that the novel formulation of the present invention has an independent effect.

Example 7

Crystallization Study

Investigations on drug crystallization kinetics were also carried out for the present invention in which the novel formulation of the present invention was compared to formulations not having the novel specified ratio. The objective was to establish a correlation between crystallization kinetics of the novel formulations of the present invention ("slow" or "fast" crystallization rate) with in vitro permeation and biodistribution results, and therefore to determine the partner/surfaces transfer potential of the formulations ("low" or "high" potential).

Different active compounds were evaluated in formulations containing the invention herein disclosed in comparison to formulations without containing the invention. The invention relates to the use of certain combination of vehicles which enhance or promote drug uptake from the skin while minimizing the amounts of skin residual after application of the drug product onto the skin.

Microscopic examination was done on several gel formulations containing the invention herein described and an active compound, compared to formulations which do not contain the invention and the same active compound. Placebo formulations were used for blank comparison as well.

An androgen compound, testosterone (octanol:water partition coefficient, or Log P about 3.3) and minoxidil (Log P about 1.2, thus less lipophilic than testosterone) were used as drug models to exemplify the invention.

An aliquot (1 mL) of the tested formulations was placed on a glass plate and immediately spread with the help of a cover slip to form a homogenous layer of gel. Glass plates holding the sample were, in all cases, let evaporated at controlled room temperature (25° C.) and observations and pictures were made at different times of exposure.

Picture illustrated herein in FIGS. 5a through 5h were taken under the same conditions, i.e., same time points (typically less than 5 minutes; 30 minutes; 2 hours for fast-crystallizing formulations or 4 hours for slow-crystallizing formulations; more than 8 hours in some case), same magnification (total ×6.5), same location: the glass plate was positioned once when initiating the study, and then was not further moved until the completion of the study. Some slight differences in contrast and texture are imputable to solvent evaporation.

FIGS. 5a-5h show the crystallization status of some formulations not containing the present invention 30 minutes after spreading of the formulations on the glass plate.

Crystallization of Testosterone Formulations

A comparative study focusing on the crystallization rate of testosterone formulations was undertaken in which the rate of crystallization of testosterone formulations of the present invention were compared to other testosterone formulations not comprising the present invention. In this regard, formulations (solutions or semi-solid) were spread over a cover glass and were observed under a microscope for the occurrence of crystal formation.

In the first study, the Gel formulation of Example A was compared to the Gel formulation of Example B for crystallization rate. Example A was ANDROGEL® a 1% testosterone gel marketed in US for male hypogonadism. The ANDROGEL® composition is as follows:

| Ingredient | % w/w |
| --- | --- |
| Testosterone | 1.00 |
| Carbomer C980 NF | 0.90 |
| Isopropyl myristate | 0.50 |
| Ethanol 96% | 71.4 |
| Sodium Hydroxide | 4.72 |
| Purified water | q.s. |

Example A

Composition of Androgel®

Androgel® (Example A), which does not comprise the present invention was compared with Example B, which also does not comprise the present invention. As noted below, Example B is a testosterone gel comprising a diethylene glycol monoethyl ether and propylene glycol in a weight ratio (TC:PG) of 1:1.2. Example A does not comprise either a diethylene glycol monoethyl ether nor propylene glycol.

| Ingredient | % w/w |
| --- | --- |
| Testosterone | 1.00 |
| Carbomer C980 NF | 1.20 |
| Diethylene glycol monoethyl ether (TRANSCUTOL ®, "TC") | 5.00 |
| Propylene glycol ("PG") | 6.00 |
| Disodium edetate | 0.06 |
| Ethanol 96% | 47.5 |
| Triethanolamine | 0.35 |
| Purified water | q.s. |

Results of Example A compared to Example B.

Crystallization was observed in Example A after 10 minutes of application of the gel formulation to the glass cover. Likewise, crystallization was also observed in Example B in 10 minutes. Thus, no significant difference in the crystallization rate was observed between Example A, ANDROGEL®, and the gel formulation of Example B, which comprises diethylene glycol monoethyl ether and propylene glycol in a 1:1.2 weight ratio.

A comparison study was also undertaken for solution formulations Examples C and D, represented below.

Example C

| Ingredient | % w/w |
| --- | --- |
| Testosterone | 1.00 |
| Isopropyl myristate | 0.50 |
| Ethanol 96% | 71.4 |
| Purified water | q.s. |

Example D

| Ingredient | % w/w |
| --- | --- |
| Testosterone | 1.00 |
| Diethylene glycol monoethyl ether (TRANSCUTOL ®, "TC") | 5.00 |
| Propylene glycol ("PG") | 6.00 |
| Disodium edetate | 0.06 |
| Ethanol 96% | 47.5 |
| Purified water | q.s. |

Crystallization was observed in Example C after only one minute, and in Example D after four minutes. Thus, formulations containing diethylene glycol monoethyl ether and propylene glycol in a 1:1.2 weight ratio do not differ significantly from reference example A, either as a gel formulation or as a solution formulation. A third comparative study was undertaken in which the propylene glycol was increased from 6.00% ww to 20% ww in Examples E and F. (The viscosity was adjusted to the ANDROGEL®; about 8000 cP).

| EXAMPLE E | |
| --- | --- |
| Ingredient | % w/w |
| Testosterone | 1.00 |
| Carbomer C980 NF | 0.60 |
| Diethylene glycol monoethyl ether (TRANSCUTOL ®, "TC") | 5.00 |
| Propylene glycol ("PG") | 20.0 |
| Disodium edetate | 0.06 |
| Ethanol 96% | 47.5 |
| Triethanolamine | 0.35 |
| Purified water | q.s. |

| EXAMPLE F: Solution | |
| --- | --- |
| Ingredient | % w/w |
| Testosterone | 1.00 |
| Diethylene glycol monoethyl ether (TRANSCUTOL ®, "TC") | 5.00 |
| Propylene glycol ("PG") | 20.0 |
| Disodium edetate | 0.06 |
| Ethanol 96% | 47.5 |
| Purified water | q.s. |

Crystallization was not observed in Example E after four hours of application of the formulation to a glass cover. Crystallization was observed after 30 minutes in Example F.

Thus, when both the gel formulation and the solution formulation comprise diethylene glycol monoethyl ether and propylene glycol in a ratio of 1:4, the crystallization rate of both formulations were significantly lower compared to other examples tested.

What is claimed is:

1. A transdermal or transmucosal non-occlusive pharmaceutical formulation that contains testosterone as active ingredient; and a solvent system present in an amount sufficient to solubilise the active ingredient, wherein the solvent system consists essentially of:
   (i) a pharmaceutically acceptable monoalkyl ether of diethylene glycol present in an amount of between about 1.36% and 7.5% by weight of the solvent system;
   (ii) a pharmaceutically acceptable glycol present in an amount of between about 13.64% and 30% by weight of the solvent system, provided that the monoalkyl ether of diethylene glycol and the glycol are present in a weight ratio of 1:4 to 1:10; and (iii) a mixture of a C2 to C4 alcohol and water which mixture is present in an amount of between about 40% and 98% of the solvent system, wherein the C2 to C4 alcohol is present in an amount of about 5% to 80% of the mixture, and the water is present in an amount of about 20% to 95% of the mixture;

wherein the formulation does not include additional permeation enhancers, and provided that the monoalkyl ether of diethylene glycol and the glycol in combination are present in amount of at least 15% and no more than 37.5% of the solvent system, so that, compared to formulations containing the same components but in different amounts and ratios, the present solvent system (a) inhibits crystallization of the at least one active ingredient on a skin or mucosal surface of a mammal, (b) reduces or prevents transfer of the formulation to clothing or to another being, (c) modulates biodistribution of the at least one active ingredient within different layers of skin, (d) facilitates absorption of the at least one active ingredient by a skin or a mucosal surface of a mammal or (e) provides a combination of one or more of (a) through (d).

2. The pharmaceutical formulation of claim 1, wherein the monoalkyl ether of diethylene glycol is selected from the group consisting of diethylene glycol monomethyl ether and diethylene glycol monoethyl ether and mixtures thereof.

3. The pharmaceutical formulation of claim 1, wherein the glycol is selected from the group consisting of propylene glycol, dipropylene glycol and mixtures thereof.

4. The pharmaceutical formulation of claim 1, wherein the C2 to C4 alcohol is selected from the group consisting of ethanol, propanol, isopropanol, 1-butanol, 2-butanol and mixtures thereof.

5. The pharmaceutical formulation according to claim 1 which includes an agent selected form the group consisting of gelling agents, preservatives, antioxidants, buffers, humectants, sequestering agents, moisturizers, surfactants, emollients and any combination thereof.

6. The pharmaceutical formulation of claim 1, wherein the testosterone is present in the formulation in an amount of about 1% by weight.

7. The pharmaceutical formulation of claim 1, wherein the pharmaceutically acceptable monoalkyl ether of diethylene glycol is diethylene glycol monoethyl ether and is present in an amount of at least about 5% by weight of the solvent system; the pharmaceutically acceptable glycol is propylene glycol and is present in an amount of at least about 20% by weight of the solvent system; and the monoethyl ether of diethylene glycol and the propylene glycol in combination are present in amount of at least 25% by weight of the solvent system.

8. The pharmaceutical formulation of claim 7, wherein the C2 to C4 alcohol is ethanol and is present in an amount of between about 15% and 65% by weight of the solvent system.

9. A transdermal or transmucosal non-occlusive pharmaceutical formulation consisting of:

testosterone as active ingredient;

an agent selected form the group consisting of gelling agents, preservatives, antioxidants, buffers, humectants, sequestering agents, moisturizers, surfactants, emollients and any combination thereof; and a solvent system present in an amount sufficient to solubilise the active ingredient, wherein the solvent system consists of:

(i) a pharmaceutically acceptable monoalkyl ether of diethylene glycol present in an amount of 5% to 7.5% by weight of the solvent system;

(ii) a pharmaceutically acceptable glycol of propylene glycol present in an amount of 20% to 30% by weight of the solvent system, provided that the monoalkyl ether of diethylene glycol and the glycol are present in a weight ratio of 1:4 to 1:6; and (iii) a mixture of a C2 to C4 alcohol and water which mixture is present in an amount of between about 40% and 98% of the solvent system, wherein the C2 to C4 alcohol is present in an amount of about 5% to 80% of the mixture, and the water is present in an amount of about 20% to 95% of the mixture;

wherein the formulation does not include fatty alcohols, fatty esters or fatty acids, and the monoalkyl ether of diethylene glycol and the glycol in combination are present in amount of at least 25% and no more than 37.5% of the solvent system, so that, compared to formulations containing the same components but in different amounts and ratios, the present solvent system (a) inhibits crystallization of the at least one active ingredient on a skin or mucosal surface of a mammal, (b) reduces or prevents transfer of the formulation to clothing or to another being, (c) modulates biodistribution of the at least one active ingredient within different layers of skin, (d) facilitates absorption of the at least one active ingredient by a skin or a mucosal surface of a mammal or (e) provides a combination of one or more of (a) through (d).

10. The pharmaceutical formulation of claim 9, wherein the C2 to C4 alcohol is ethanol and is present in an amount of between about 15% and 65% by weight of the solvent system.

11. The pharmaceutical formulation of claim 9, wherein the testosterone is present in the formulation in an amount of about 1% by weight.

* * * * *